(12) United States Patent
Horn et al.

(10) Patent No.: US 9,359,634 B2
(45) Date of Patent: Jun. 7, 2016

(54) FAST REACTION KINETICS OF ENZYMES HAVING LOW ACTIVITY IN DRY CHEMISTRY LAYERS

(75) Inventors: Carina Horn, Biblis (DE); Claudia Gaessler-Dietsche, Schriesheim (DE); Dieter Heindl, Munich (DE); Joachim Hoenes, Zwingenberg (DE); Thomas Meier, Munich (DE); Rainer Schmuck, Benediktbeuern (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 165 days.

(21) Appl. No.: 13/210,564

(22) Filed: Aug. 16, 2011

(65) Prior Publication Data

US 2014/0322737 A1    Oct. 30, 2014

Related U.S. Application Data

(63) Continuation of application No. PCT/EP2010/051801, filed on Feb. 12, 2010.

(30) Foreign Application Priority Data

Feb. 19, 2009    (WO) .................. PCT/EP2009/001206

(51) Int. Cl.
| | |
|---|---|
| C12Q 1/54 | (2006.01) |
| C12N 11/00 | (2006.01) |
| C12N 11/02 | (2006.01) |
| C12N 11/14 | (2006.01) |
| C12N 9/04 | (2006.01) |
| C12Q 1/32 | (2006.01) |

(52) U.S. Cl.
CPC ............... *C12Q 1/54* (2013.01); *C12N 9/0006* (2013.01); *C12N 11/00* (2013.01); *C12N 11/02* (2013.01); *C12N 11/14* (2013.01); *C12Q 1/32* (2013.01)

(58) Field of Classification Search
None
See application file for complete search history.

(56) References Cited

U.S. PATENT DOCUMENTS

| | | |
|---|---|---|
| 5,801,006 A | 9/1998 | Kaufamn |
| 7,553,615 B2 | 6/2009 | Heindl et al. |
| 2004/0023330 A1 | 2/2004 | Sode |

(Continued)

FOREIGN PATENT DOCUMENTS

| | | |
|---|---|---|
| JP | 2003-310274 A | 11/2003 |
| WO | WO 98/33936 | 8/1998 |

(Continued)

OTHER PUBLICATIONS vonKetteler et al., "Fluorescence properties of carba nicotinamide adenine dinucleotide for glucose sensing", ChemPhysChem, vol. 13, pp. 1302-1306, 2012.*

(Continued)

*Primary Examiner* — Robert Mondesi
*Assistant Examiner* — Richard Ekstrom
(74) *Attorney, Agent, or Firm* — Roche Diabetes Care, Inc.

(57) ABSTRACT

The present invention concerns a method for determining an analyte as well as a diagnostic element suitable therefore. In one particular form, a method for determining an analyte includes contacting a sample containing the analyte with a diagnostic element comprising a dry reagent layer. The dry reagent layer contains a mutated dehydrogenase which is specific for the analyte and an artificial coenzyme. The method also includes determining at least one of analyte presence and an amount of the analyte.

13 Claims, 10 Drawing Sheets

(56) References Cited

U.S. PATENT DOCUMENTS

| | | |
|---|---|---|
| 2005/0214891 A1 | 9/2005 | Horn et al. |
| 2008/0213809 A1 | 9/2008 | Heindl et al. |
| 2011/0143416 A1 | 6/2011 | Horn et al. |

FOREIGN PATENT DOCUMENTS

| | | |
|---|---|---|
| WO | WO 01/49247 | 7/2001 |
| WO | 0194370 | 12/2001 |
| WO | WO 2005/045016 | 5/2005 |
| WO | WO 2005/084530 | 9/2005 |
| WO | WO 2007/012494 A1 | 2/2007 |
| WO | WO 2009/103540 A1 | 8/2009 |
| WO | WO 2010094632 A1 * | 8/2010 |

OTHER PUBLICATIONS

Guo et al., "Protein tolerance to random amino acid change", Proceedings of the National Academy of Sciences USA, vol. 101, No. 25, pp. 9205-9210, 2004.*

International Search Report corresponding to PCT/EP2010/051801.

Biak et al.; Cooperative Effect of Two Surface Amino Acid Mutations (Q252L and E170K) in Glucose Dehydrogenase from Bacillus megaterium IWG3 on Stabilizations of Its Oligomeric State; Applied and Environmental Microbiology, Jun. 2005; p. 3285-3293; American Society for Microbiology; 2005.

Vazquez-Figueroa et al.; Development of a Thermostable Glucose Dehydrogenase by a Structure-Guided Consensus Concept; ChemBioChem 2007, 8, 2295-2301 Inter-Science.

Hutchinson et al.; Synthesis of carbocyclic NAD+ containing a methylenebisphosphonate linkage for the investigation of ADP-ribosyl cyclase; Chem. Commun., 1996 p. 2765-2766.

Slama et al.; Inhibition of NAD Glycohydrolase and ADP-ribosyl Transferases by Carbocyclic Analogues of Oxidized Nicotinamide Adenine Dinucleotide; 1989 American Chemical Society; Biochemistry 1989 28, 7688-7694; XP 002502968.

Slama et al.; Carbanicotinamide Adenine Dinucleotide: Synthesis and Enzymological Properties of a Carbocyclic Analogue of Oxidized Nicotinamide Adenine Dinucleotide; 1988 American Chemical Society; Biochemistry 1988, 27, 183-193.

International Search Report corresponding to PCT/EP2009/001206.

Liao et al.; Characteristics of magnetic nanoparticles-bound YADH in water/AOT/isooctane microemulsions; Journal of Molecular Catalysis B: Enzymatic 18 (2002) 81-87.

Van Den Heuvel et al.; Coenzyme Binding During Catalysis is Beneficial for the Stability of 4-Hydroxyacetophenone Monooxygenase; The Journal of Biological Chemistry, Sep. 16, 2005, vol. 280. No. 37, p. 32115-32121 and in particular p. 32119, right-hand column, lines 4-5, 16-18.

Pan et al.; Coenzyme Stabilization of Rat Liver Cystathionine Synthetase and Cystathionase, Journal of the Chinese Biochemical Society, vol. 3, No. 1 pp. 1-8, 1974.

Bertoldi et al.; Folding pathway of the pyridoxal 5'-phosphatase C-S lyase MalY from *Escherichia coli*, Biochem. J. 389, pp. 885-898, 2005.

Tramper et al.; Progress in Biotechnology 8, Biocatalysis in Non-Conventional Media, Proceedings of an International Symposium Noordwijkerhout, pp. 739-745, Apr. 26-29, 1992.

Does Coenzyme Binding Determine Enzyme Stability?, Nutrition Reviews, vol. 36, No. 8, pp. 251-524, Aug. 1978.

Everse et al.; The Pyridine Nucleotide Coenzymes, Academic Press New York, London, Chapter 3, pp. 56-65, 1982.

Everse et al.; The Pyridine Nucleotide Coenzymes, Academic Press New York, London, Chapter 4.

Kaplan et al.; Chemistry and Properties of the 3-Acetylpyridine Analogue of Diphosphopyridine Nucleotide, J. Biol. Chem. 221, pp. 823-832, Dec. 5, 1955.

Slama et al.; Carbanicotinamide Adenine Dinucleotide: Synthesis and Enzymological Properties of a Carbocyclic analogue of Oxidized Nicotinamide Adenine Dinucleotide, Biochemistry, vol. 27, pp. 183-193, 1988.

Nagao et al.; Stability-increasing mutants of glucose dehydrogenase; FEBS Letters, vol. 253, No. 1, 2, pp. 113-116, Aug. 1989.

* cited by examiner

FAST REACTION KINETICS OF ENZYMES HAVING LOW ACTIVITY IN DRY CHEMISTRY LAYERS

CROSS-REFERENCE TO RELATED APPLICATIONS

This application is a continuation of International Application No. PCT/EP2010/051801 filed Feb. 12, 2010, which claims priority to International Application No. PCT/EP2009/001206 filed Feb. 19, 2009. Each of the referenced applications is incorporated herein by reference in its entirety.

FIELD OF THE INVENTION

The present invention concerns a method for determining an analyte and a suitable diagnostic element therefore.

BACKGROUND

Diagnostic elements are important components of clinically relevant analytical methods. In this connection, the primary focus is on the measurement of analytes, e.g. metabolites or substrates, which are for example determined directly or indirectly with the aid of an enzyme which is specific for the analyte. In this case, the analytes are converted with the aid of an enzyme-coenzyme complex and subsequently quantified. In this process, the analyte to be determined is brought into contact with a suitable enzyme, a coenzyme and optionally a mediator and the coenzyme is physicochemically changed by the enzymatic reaction, e.g. oxidized or reduced. If a mediator is additionally used, this mediator usually transfers the electrons released during the reaction of the analyte from the reduced coenzyme to an optical indicator or to the conductive components of an electrode so that the process can for example be detected photometrically or electrochemically. A calibration yields a direct relationship between the measured value and the concentration of the analyte to be determined.

Diagnostic elements known from the prior art are characterized by a limited shelf-life and by special requirements for the environment, e.g. cooling or dry storage, in order to achieve this shelf-life. Thus, in certain forms of application, e.g. in the case of tests which are carried out by the end user himself such as blood glucose self-monitoring, erroneous results may occur due to a false, unnoticed incorrect storage of the measurement system which can hardly be recognized by the consumer and may lead to an erroneous treatment of the respective disease. The erroneous results are primarily due to the fact that the enzymes, coenzymes and mediators used in such diagnostic elements generally react sensitively to moisture and heat and are inactivated over time.

A known measure which is used to increase the stability of diagnostic elements is the use of stable enzymes, for example the use of enzymes from thermophilic organisms. Furthermore, enzymes can be stabilized by chemical modification, and in particular by cross-linking. Moreover, enzyme stabilizers such as for example trehalose, polyvinyl pyrrolidone and serum albumin can also be added, or the enzymes can be enclosed in polymer networks by photopolymerization for example.

Another method of stabilizing enzymes is by means of mutations that are introduced site-specifically or non-site-specifically. In this connection, the use of recombinant techniques which specifically influence the properties of the corresponding enzyme by means of a targeted change in the DNA coding for an enzyme, have proven to be particularly suitable.

Baik et al. (Appl. Environ. Microbiol (2005), 71, 3285) describe the isolation and characterization of three mutants of glucose dehydrogenase from *Bacillus megaterium* which contain the amino acid substitutions E170K, Q252L or E170K/Q252L. Whereas the mutants E170K and Q252L only have a low stability at low salt concentrations and high pH values, the double mutant exhibits a significantly increased stability under the test conditions due to an enhanced interaction at the dimer-dimer interface.

Vázquez-Figueroa et al. (ChemBioChem (2007), 8, 2295) disclose the development of a thermostable glucose dehydrogenase which comprises introducing amino acid substitutions at positions 155, 170 and 252 of the glucose dehydrogenase from *Bacillus subtilis, Bacillus thuringiensis* and *Bacillus licheniformis*. In this connection, it is stated that the mutations E170K and Q252L, individually as well as in combination, result in a stabilization of glucose dehydrogenase from *Bacillus subtilis*.

However, when stabilized enzymes which are genetically modified compared to the wild-type variant are used, the problem arises that they usually have a considerably lower activity than the corresponding wild-type enzyme, and thus cause a lower substrate turnover per unit of time. If one takes into consideration the fact that enzymes having a high specific activity are preferably used in clinical and diagnostic chemistry such as in the detection of blood glucose, the use of stabilized enzymes is often an unacceptable alternative to the use of native enzymes.

Another difficulty is that high enzyme activities which correlate with a high substrate turnover per unit of time are usually only achieved with the respective native coenzyme in each case. If an artificial coenzyme is used instead of the native coenzyme, then the enzyme activity is usually drastically reduced and the rate of turnover with the substrate decreases accordingly.

SUMMARY

One object of the present invention is to provide a stable diagnostic element, in particular for determining glucose, in which the disadvantages of the prior art are at least partially eliminated. In particular, the diagnostic element should ensure a high turnover rate of substrate while at the same time ensuring a high stability of the enzyme as well as of the coenzyme.

In one embodiment, a method for determining an analyte includes the following steps:
(a) contacting a sample containing the analyte with a diagnostic element comprising a dry reagent layer which contains:
  (i) a mutated dehydrogenase which is specific for the analyte and
  (ii) an artificial coenzyme, and
(b) determining at least one of analyte presence and an amount of the analyte.

In a further embodiment, a diagnostic element for determining an analyte includes a dry reagent layer which contains:
(a) a mutated dehydrogenase which is specific for the analyte, and
(b) an artificial coenzyme.

With regard to more particular embodiments of the diagnostic element as well as of the mutated dehydrogenase contained therein or the artificial coenzyme contained therein, reference is made to the embodiments in conjunction with the description provided below.

BRIEF DESCRIPTION OF THE DRAWINGS

The invention is further elucidated by the following figures, description and examples.

FIG. 1 is a graphical illustration of kinetics of wild type glucose dehydrogenase from Bacillus subtilis in the presence of NAD/NADH as the coenzyme at glucose concentrations of 0.0 mg/dl, 35.2 mg/dl, 54.2 mg/dl, 146.6 mg/dl, 249.0 mg/dl, 338.6 mg/dl and 553.6 mg/dl (shown from top to bottom).

FIG. 5 is a graphical illustration of kinetics of the conversion of glucose in the presence of wild type glucose dehydrogenase and NADH at various glucose concentrations.

DETAILED DESCRIPTION

Figure 1A:
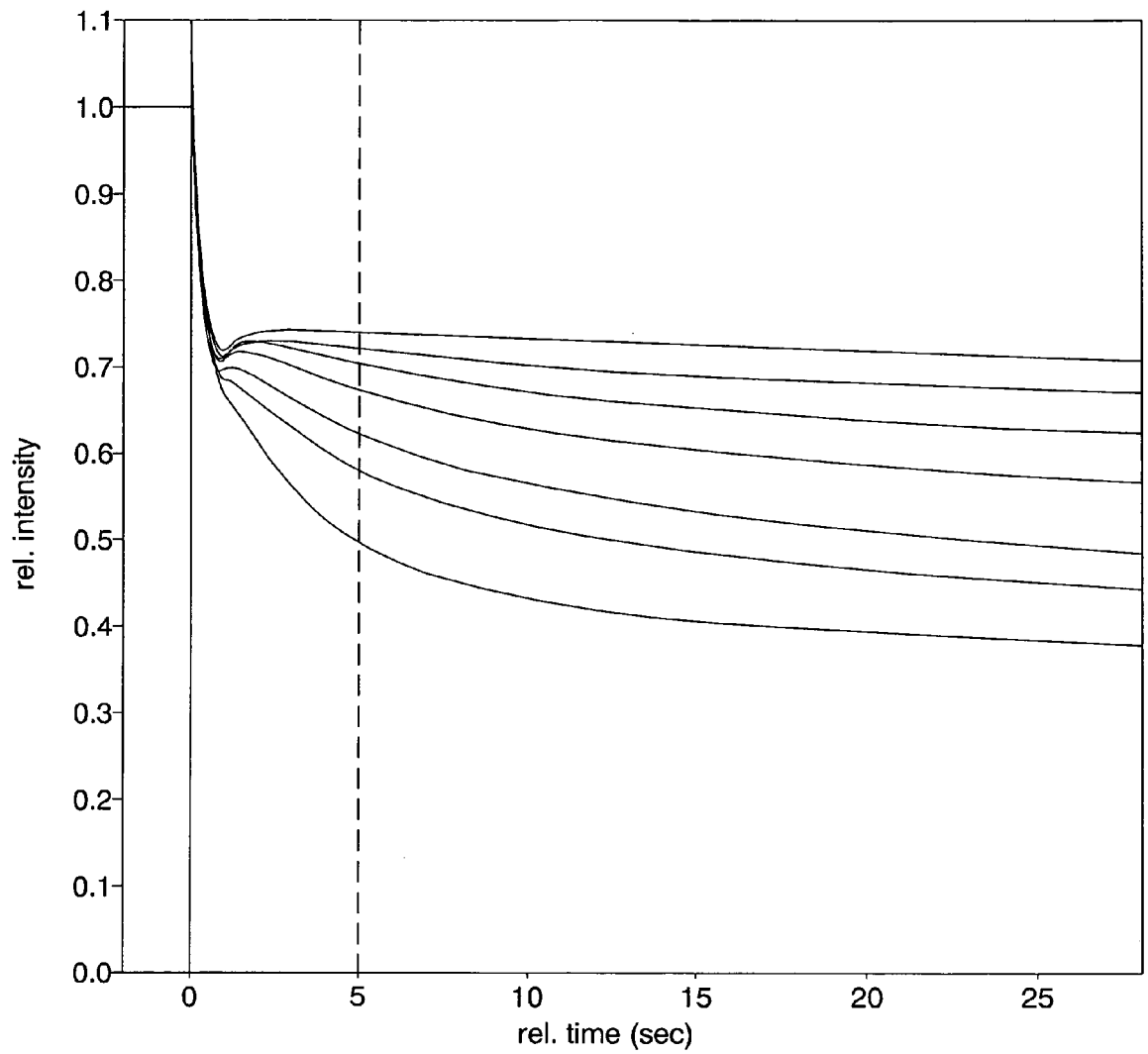
FIG. 1A: enzyme activity 1556.2 kU/100 g mass
Figure 1B:
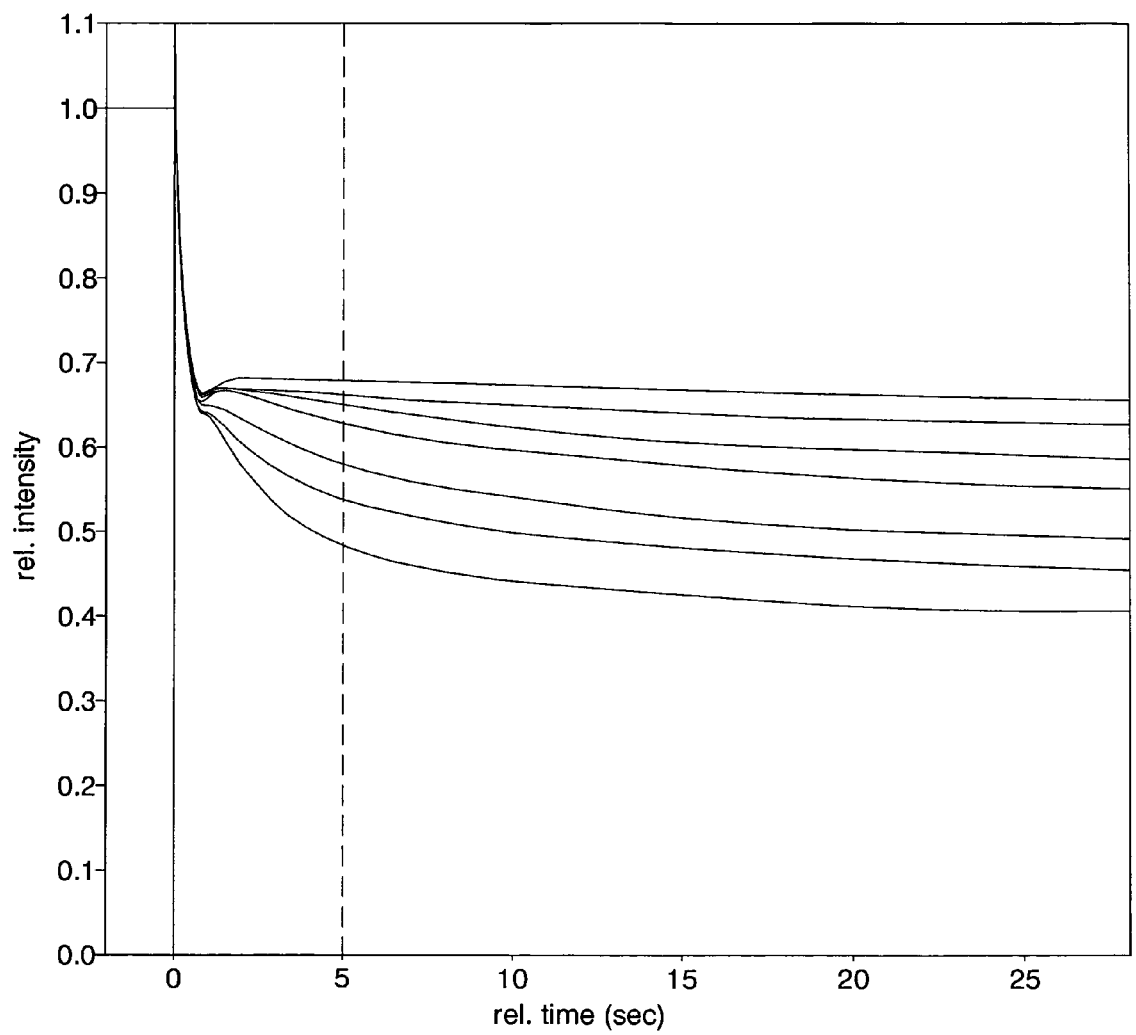
FIG. 1B: enzyme activity 1004.0 kU/100 g mass
Figure 1C:
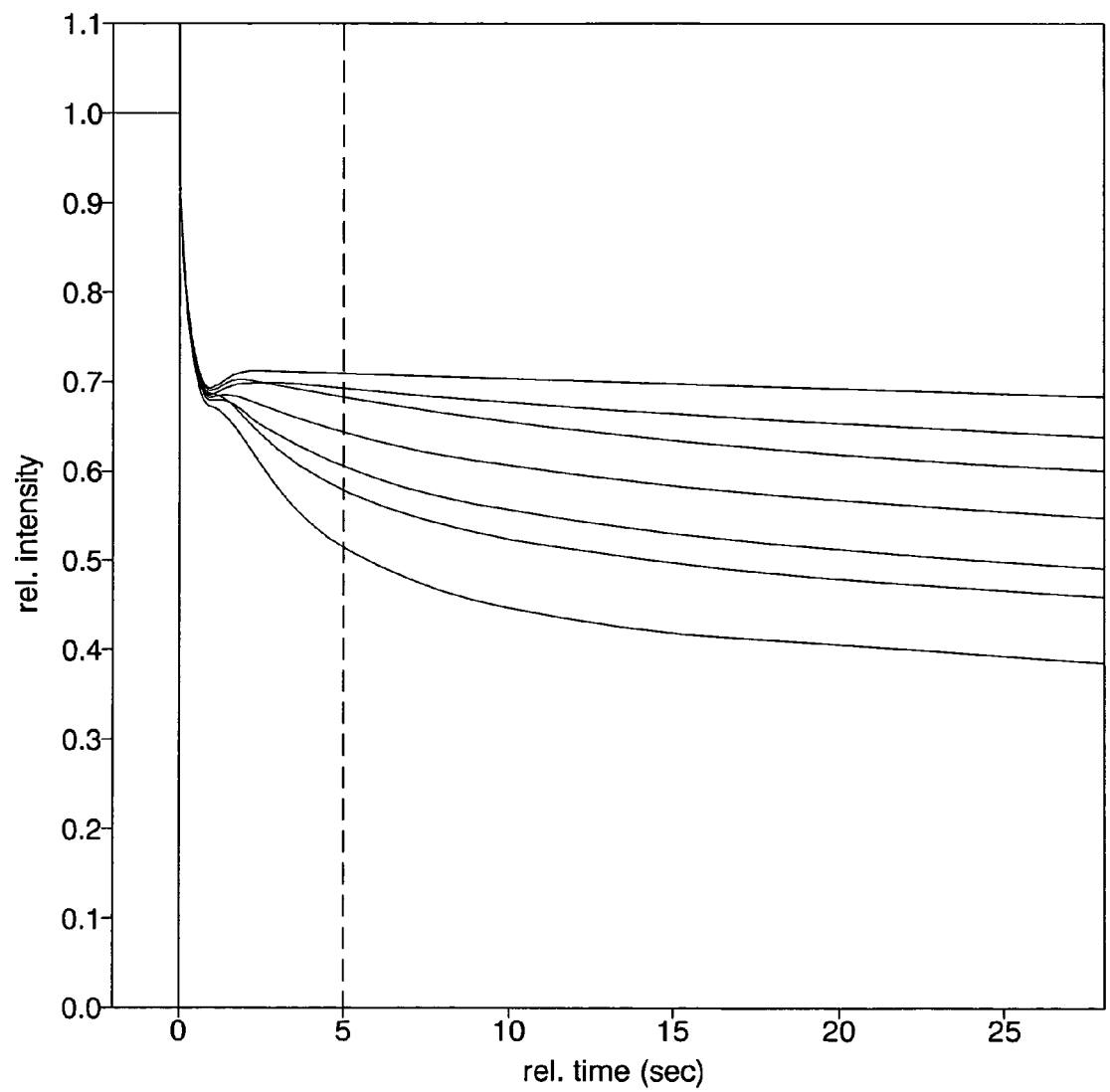
FIG. 1C: enzyme activity 502.0 kU/100 g mass
Figure 1D:
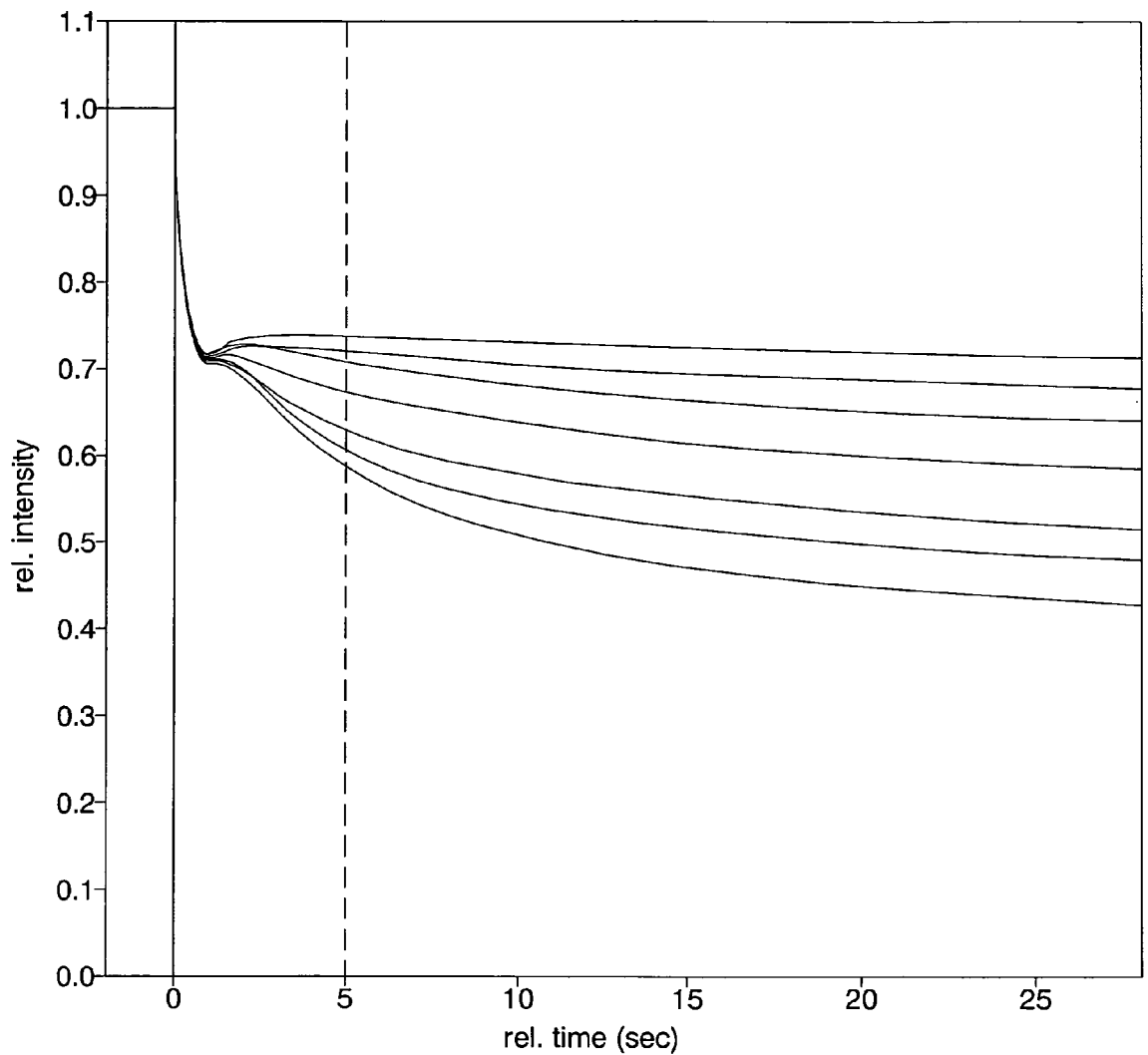
FIG. 1D: enzyme activity 251.0 kU/100 g mass
Figure 1E:
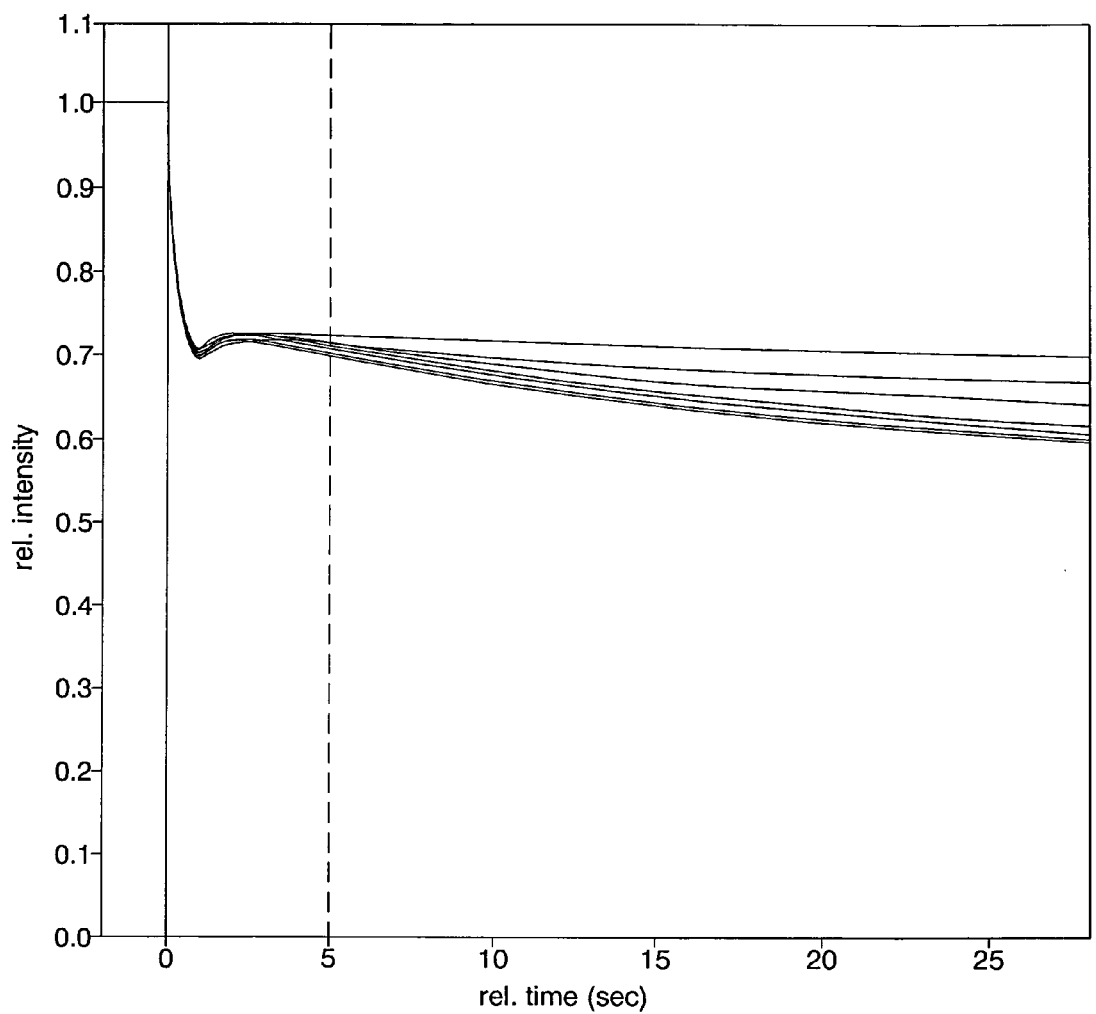
FIG. 1E: enzyme activity 25.10 kU/100 g mass.

In one embodiment, a method for determining an analyte includes the following steps:
(a) contacting a sample containing the analyte with a diagnostic element comprising a dry reagent layer which contains:
 (i) a mutated dehydrogenase which is specific for the analyte and
 (ii) an artificial coenzyme, and
(b) determining at least one of analyte presence and an amount of the analyte.

In a further embodiment, a diagnostic element for determining an analyte includes a dry reagent layer which contains:
(a) a mutated dehydrogenase which is specific for the analyte, and
(b) an artificial coenzyme.

It has been surprisingly discovered that mutated dehydrogenases, which have extremely low activities in the presence of an artificial coenzyme in the cuvette test, exhibit more rapid kinetics in diagnostic elements with dry reagent layers such as in test strips, and yield at least as much turnover as in the presence of the native coenzyme (wild type coenzyme). The reason for this is presumably due to the fact that at high concentrations of ingredients other factors than the activity of the enzyme decisively influence the turnover rate, and in this connection the state of complex formation between enzyme, coenzyme, reduced coenzyme, analyte and oxidized analyte appears to be particularly crucial.

In this respect, one method according to the invention provides in one embodiment that the turnover rate of the analyte in the diagnostic element described herein is equal to or higher than the turnover rate of the analyte in a corresponding diagnostic element which comprises the corresponding wild type coenzyme instead of the artificial coenzyme. In one form, the turnover rate of the analyte in a diagnostic element used according to the invention is increased by at least 20%, and more particularly by at least 50% or by at least 100%. In one form for example, the turnover rate of the analyte is increased by 100% to 200% compared to the turnover rate of the analyte in a diagnostic element comprising the wild type coenzyme.

The terms "mutated dehydrogenase" or "dehydrogenase mutant" as used in the present application refer to a genetically modified variant of a native dehydrogenase (wild type dehydrogenase) which has an amino acid sequence that is modified compared to the wild type dehydrogenase while having the same number of amino acids, i.e. which differs by at least one amino acid from the wild type dehydrogenase.

The mutated dehydrogenase can be obtained by mutation from a wild type dehydrogenase derived from any biological source, where the term "biological source" in the sense of this invention encompasses prokaryotes such as bacteria as well as eukaryotes such as mammals and other animals. The introduction of the mutation(s) can take place site-specifically or non-site-specifically, preferably site-specifically using recombinant methods known in the art, resulting in at least one amino acid substitution within the amino acid sequence of the native dehydrogenase in accordance with the respective requirements and conditions.

A dehydrogenase mutant obtained in this manner and used in one method according to the invention preferably has an increased thermal or/and hydrolytic stability compared to the corresponding wild type dehydrogenase. Examples of such mutants are described among others in Baik (Appl. Environ. Microbiol. (2005), 71, 3285), Vázquez-Figueroa (ChemBioChem (2007), 8, 2295) as well as in WO 2005/045016 A2, the disclosures of which are herewith explicitly incorporated by reference.

In one form, a mutated dehydrogenase in the sense of the present invention has a reduced specific enzyme activity compared to the corresponding wild type dehydrogenase. The term "specific enzyme activity" (stated in U/mg enzyme) as used in the present application refers to the amount of substrate which is converted under predefined conditions per minute and per milligram of enzyme. On the other hand, the term "lyophilisate activity" refers to the amount of substrate which is converted under predetermined conditions per minute and per milligram of lyophilisate comprising the enzyme in combination with auxiliary substances.

The mutated dehydrogenase used in one or more methods according to the invention is a nicotinamide adenine dinucleotide (NAD/NADH)-dependent or nicotinamide adenine dinucleotide phosphate (NADP/NADPH)-dependent mutated dehydrogenase which is selected from a mutated alcohol dehydrogenase (EC 1.1.1.1; EC 1.1.1.2), a mutated L-amino acid dehydrogenase (1.4.1.5), a mutated glucose dehydrogenase (EC 1.1.1.47), a mutated glucose-6-phosphate dehydrogenase (EC 1.1.1.49), a Mutated glycerol dehydrogenase (EC 1.1.1.6), a mutated 3-hydroxybutyrate dehydrogenase (EC 1.1.1.30), a mutated lactate dehydrogenase (EC 1.1.1.27; EC1.1.1.28), a mutated malate dehydrogenase (EC 1.1.1.37) and a mutated sorbitol dehydrogenase. In one particular form, the mutated dehydrogenase is a mutated glucose dehydrogenase (EC 1.1.1.47).

If a mutated glucose dehydrogenase is used within the scope of the present invention, it can contain (a) modified amino acid(s) compared to the corresponding wild type glucose dehydrogenase basically at any position in its amino acid sequence. In one form, the mutated glucose dehydrogenase comprises a mutation at at least one of the positions 170 and 252 of the amino acid sequence of the wild type glucose dehydrogenase. In another form, the mutated glucose dehydrogenase includes mutations at position 170 and position 252. It has proven to be advantageous when the mutated glucose dehydrogenase contains no further mutations in addition to these mutations.

The mutation at positions 170 or/and 252 can basically comprise any amino acid substitution which results in a stabilization, e.g. in an increase in the thermal or/and hydrolytic stability of the wild type dehydrogenase. In one form, the mutation at position 170 comprises an amino acid substitution of glutamic acid by arginine or lysine, in particular an amino acid substitution of glutamic acid by lysine, whereas with reference to position 252 the mutation comprises an amino acid substitution of lysine by leucine.

In one or more forms, the wild type glucose dehydrogenases used to produce the above-mentioned mutants of glucose dehydrogenase are derived from a bacterium. In one particular form, a glucose dehydrogenase is derived from *Bacillus megaterium, Bacillus subtilis* or *Bacillus thuringiensis*. In another more particular form, a glucose dehydrogenase is derived from *Bacillus subtilis*. In one specific embodiment, a mutated glucose dehydrogenase GlucDH_E170K_K252L having the amino acid sequence shown in SEQ ID NO:1 obtained by mutation of wild type glucose dehydrogenase from *Bacillus subtilis* is used.

According to the invention, the diagnostic elements described herein furthermore comprise an artificial coenzyme in addition to a mutated dehydrogenase which is specific for the analyte. An artificial coenzyme within the sense of the present invention is a coenzyme which is chemically modified compared to the native coenzyme and has a higher stability towards moisture, temperatures especially in the range of 0° C. to 50° C., acids and bases especially in the range pH 4 to pH 10 or/and nucleophiles such as alcohols or amines at atmospheric pressure compared to the native coenzyme, and is thus able to exhibit its activity over a longer period than the native coenzyme under identical environmental conditions.

In one form, the artificial coenzyme preferably has a higher hydrolytic stability compared to the native coenzyme, with a complete resistance to hydrolysis under the test conditions being particularly preferred in one or more forms. The artificial coenzyme can have a reduced binding constant for the dehydrogenase compared to the native coenzyme, e.g. a binding constant that is reduced by a factor 2 or more.

More particular examples of artificial coenzymes which can be used within the scope of the method according to the invention are artificial NAD(P)/NAD(P)H compounds, i.e. chemical derivatives of native nicotinamide adenine dinucleotide (NAD/NADH) or native nicotinamide adenine dinucleotide phosphate (NADP/NADPH) or the compound of formula (I)

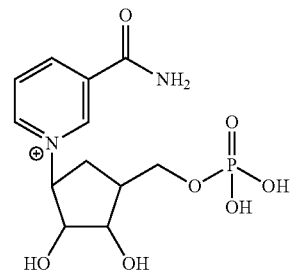

If the artificial coenzyme is an artificial NAD(P)/NAD(P)H compound, the artificial NAD(P)/NAD(P)H compound preferably comprises a 3-pyridine carbonyl or a 3-pyridine thiocarbonyl residue which is linked without a glycosidic bond to a phosphorus-containing residue such as for example a phosphate residue via a linear or cyclic organic residue, in particular via a cyclic organic residue.

In one form, the artificial coenzyme is particularly selected from a compound of the general formula (II):

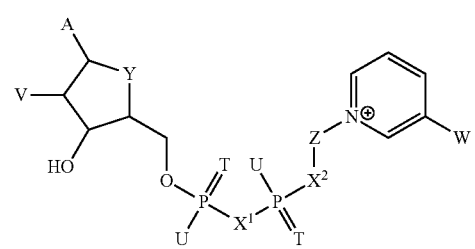

in which
A=adenine or an analogue thereof,
T=in each case independently denotes O or S;
U=in each case independently denotes OH, SH, $BH_3^-$, or $BCNH_2^-$:
V=in each case independently denotes OH or a phosphate group, or two groups which form a cyclic phosphate group;
W=COOR, CON(R)$_2$, COR, or CSN(R)$_2$ where R in each case independently denotes H or $C_1$-$C_2$ alkyl;
$X^1$, $X^2$=in each case independently denote O, $CH_2$, $CHCH_3$, $C(CH_3)_2$, NH, or $NCH_3$:
Y=NH, S, O, or $CH_2$;
Z=is a linear or cyclic organic residue,
provided that Z and the pyridine residue are not linked by a glycosidic bond,
or a salt or optionally a reduced form thereof.

In one or more compounds of formula (II), Z is preferably a linear residue having 4-6 C atoms, preferably having 4 C atoms in which 1 or 2 C atoms are optionally replaced by one or more heteroatoms selected from O, S and N, or a residue comprising a cyclic group having 5 or 6 C atoms which optionally contains a heteroatom selected from O, S and N and optionally one or more substituents, and a residue $CR^4_2$, where $CR^4_2$ is bound to the cyclic group and to $X^2$, with $R^4$ being in each case independently H, F, Cl, or $CH_3$.

In one particular form, Z is a saturated or unsaturated carbocyclic or heterocyclic five-membered ring, in particular a compound of the general formula (III),

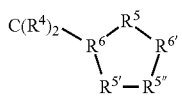

(III)

wherein a single or double bond may be present between $R^{5'}$ and $R^{5''}$, in which $R^4$=in each case independently denotes H, F, Cl, or $CH_3$;
$R^5=CR^4_2$;
$R^{5'}$=O, S, NH, $NC_1$-$C_2$ alkyl, $CR^4_2$, CHOH, or $CHOCH_3$, and $R^{5''}=CR^4_2$, CHOH, or $CHOCH_3$ if a single bond is present between $R^{5'}$ and $R^{5''}$;
$R^{5'}=R^{5''}=CR^4$, if a double bond is present between $R^{5'}$ and $R^{5''}$; and
$R^6$, $R^{6'}$=in each ease independently denote CH or $CCH_3$.

In one particular embodiment, the compounds according to the invention contain adenine or adenine analogues such as for example $C_8$-substituted and $N_6$-substituted adenine, deaza variants such as 7-deaza, aza variants such as 8-aza or combinations such as 8-deaza or 7-aza or carbocyclic analogues such as formycin, wherein the 7-deaza variants can be substituted in the 7 position by halogen, $C_{1-6}$ alkinyl, $C_{1-6}$ alkenyl or $C_{1-6}$ alkyl.

In a further embodiment the compounds contain adenosine analogues which contain for example 2-methoxydeoxyribose, 2'-fluorodeoxyribose, hexitol, altritol or polycyclic analogues such as bicycle sugars, LNA sugars and tricyclo sugars instead of ribose.

In particular, (di)-phosphate oxygens can also be isotronically replaced in the compounds of formula (II) such as e.g. $O^-$ by $S^-$ or $BH_3^-$, O by NH, $NCH_3$, or $CH_2$ and =O by =S. In one or more forms of the compounds of formula (II) according to the invention, W is preferably $CONH_2$ or $COCH_3$.

$R^5$ is preferably $CH_2$ in one or more forms of formula (III). Furthermore, it is preferred that $R^{5'}$ is selected from $CH_2$, CHOH and NH. In one particular embodiment, $R^{5'}$ and $R^{5''}$ are in each case CHOH. In yet a further embodiment, $R^{5'}$ is NH and $R^{5''}$ is $CH_2$. Another embodiment includes a compound of formula (III) in which $R^4$=H, $R^5=CH_2$, $R^{5'}=R^{5''}$=CHOH and $R^6=R^{6'}$=CH.

In one particular embodiment, the artificial coenzyme is the compound carbaNAD known from the literature (J. T. Slama, Biochemistry (1988), 27, 183 and Biochemistry (1989), 28, 7688). Other stable coenzymes which can be used according to the invention are described in WO 98/33936, WO 01/49247, WO 2007/012494, U.S. Pat. No. 5,801,006, U.S. Ser. No. 11/460,366 and the publication by Blackburn et al. (Chem. Comm. (1996), 2765), the disclosures of which are herewith explicitly incorporated by reference.

The diagnostic element used in the method according to the invention can be any diagnostic element which comprises a dry reagent layer containing the mutated dehydrogenase and the artificial coenzyme and can be wetted by the sample containing the analyte. In addition to the mutated dehydrogenase and the artificial coenzyme, the reagent layer can optionally contain further reagents which are used for the qualitative detection or quantitative determination of the analyte, such as for example a suitable mediator as well as suitable auxiliary substances or/and additives.

Diagnostic elements on which the analyte can be applied in the form of an aqueous or non-aqueous solution are preferably used within the scope of the present invention. In one particular embodiment of the invention, the diagnostic element is a test tape, a test disk, a test pad, a test strip, a test strip drum, or the diagnostic elements mentioned in WO 2005/084530 A2 to which reference is herewith explicitly made. The diagnostic elements described in the present application comprise in each case at least one test area which can be brought into contact with a sample containing the analyte and enables a qualitative or/and quantitative determination of the analyte using suitable means.

The tem) "test tape" as used herein refers to a tape-like diagnostic element which usually comprises more than one individual test area. In one form, the element comprises at least 10, 25 or 50 individual test areas. In one or more forms, the individual test areas are each arranged at a distance of a few millimeters to a few centimeters, for example at a distance of <2.5 cm from one another, and the test tape can optionally comprise marker areas between consecutive test areas to record the distance traveled during tape transport or/and for calibration. Such test tapes are for example described in EP 1739 432 A1, the disclosure of which is explicitly incorporated by reference.

The term "test disk" as used herein refers to a disk-shaped diagnostic element which can comprise one or more individual test areas, for example at least 10 individual test areas. In one embodiment, the test disk is coated with a thin layer of the test chemistry, e.g. with a layer having a thickness of about 20 μm, on which a sample of the analyte can be applied whereby an area of the test disk of greater or lesser size is wetted by the sample depending on the volume of the sample and can be used to determine the analyte. The non-wetted area of the test disk which can be partly or completely wetted due to passage of moisture through the test chemistry layer is subsequently available for further determinations of the analyte.

In one embodiment, a method according to the invention can be used to determine any biological or chemical substance which can be detected photochemically or electrochemically. In one or more forms, the analyte is preferably selected from the group consisting of malic acid, alcohol, ammonium, ascorbic acid, cholesterol, cysteine, glucose, glucose-6-phosphate, glutathione, glycerol, urea, 3-hydroxybutyrate, lactic acid, 5'-nucleotidase, peptides, pyruvate, salicylate and triglycerides. In one particular form, the analyte is glucose. In this connection, the analyte can originate from any source but in particular forms is contained in a body fluid comprising, but not limited to, whole blood, plasma, serum, lymph fluid, bile, cerebrospinal fluid, extracellular tissue fluid, urine, as well as glandular secretions such as saliva or sweat. The presence and/or the amount of an analyte in a sample from whole blood, plasma, serum or extracellular tissue fluid is preferably determined by means of the diagnostic elements described herein.

The qualitative or/and quantitative determination of the analyte can take place in any manner. For this purpose, all methods for detecting enzymatic reactions which are known from the prior art and which generate a measurable signal that can be analysed or read-out manually or by using suitable means can basically be used. Within the scope of the present invention, optical detection methods which for example comprise the measurement of absorption, fluorescence, circular dichroism (CD), optical rotation dispersion (ORD), refractometry etc. as well as electrochemical techniques are preferably used. In one or more forms, the presence and/or the amount of the analyte is particularly determined photometrically or fluorometrically, e.g. indirectly by means of a fluorometrically detectable change of the artificial coenzyme.

EXAMPLES

The following examples are for illustration purposes and are not to be construed as limiting the invention disclosed in this document to only the embodiments disclosed in these examples.

Example 1

Preparation of a Double Mutant of Glucose Dehydrogenase from *Bacillus subtilis* with Amino Acid Substitutions E170K and K252L (GlucDH_E170K_K252L)

In order to generate an enzyme which is stabilized compared to native dehydrogenase, the nucleic acid sequence of glucose dehydrogenase from *Bacillus subtilis* was introduced in the plasmid pKK177 (cloned via EcoRI and HindIII). The mutations E170K and K252L were introduced by site-specific mutagenesis firstly at position 170 and subsequently by site-specific mutagenesis at position 252 of the amino acid sequence of the wild type glucose dehydrogenase. The respective mutagenesis steps were carried out with the aid of specifically designed primers as part of a PCR reaction.

The PCR product obtained was transformed into *Escherichia coli* XL1blue MRF'. The cells were plated out, clones containing plasmid were cultured overnight and the enzyme activity was determined before and after temperature stress (stress test: 30 min at 50° C.). The results are shown in table 1.

TABLE 1

Residual activity of wild type glucose dehydrogenase from
*Bacillus subtilis* and the mutants GlucDH_E170K and
GlucDH_E170K_K252L after stress
(tested in *Escherichia coli* XL1blue MRF').

|  | residual activity after stress (%) |
|---|---|
| wild type glucose dehydrogenase | 23 |
| mutant GlucDH_E170K | 80 |
| mutant GlucDH_E170K_K252L | 130 |

Positive clones were tested before sequencing a further two times. The double mutant GlucDH_E170K_K252L obtained in this manner was transformed into the production strain *Escherichia coli* NM522 using pUBS-520 as a helper plasmid.

Example 2

Purification of the Double Mutant GlucDH_E170K_K252L 10 g biomass of each was taken up in 50 ml of a 30 mM potassium phosphate buffer pH 6.5 and disrupted at about 800 bar. After separation of the cell debris, a chromatography was carried out on DEAE sepharose (GE Healthcare Company) at a loading of <40 mg protein/ml column volume and using a linear gradient of buffer A (30 mM potassium phosphate buffer pH 6.5) to buffer B (buffer A+500 mM NaCl). The fractions which exhibited glucose dehydrogenase activity were combined and adjusted with ammonium sulfate (Aldrich Company) to a conductivity of 230 mS/cm.

After centrifugation, the clean supernatant was chromatographically separated on phenyl sepharose FF (GE Healthcare Company) at a maximum loading of 10 mg protein/ml column volume. The elution was carried out using a linear gradient of buffer A which was adjusted with ammonium sulfate to a conductivity of 230 mS/cm to pure buffer A. The fractions were tested for their enzyme activity, combined, rebuffered to a concentration of about 50 mg/ml in 60 mM potassium phosphate buffer pH 6.5, concentrated and lyophilized.

Example 3

Determination of the Activity of Wild Type Glucose Dehydrogenase from *Bacillus subtilis* and of the Double Mutant GlucDH_E170K_K252L in the Cuvette Test In order to examine the specific activity or lyophilisate activity of wild type glucose dehydrogenase from *Bacillus subtilis* as well as of the double mutant GlucDH_E170K_K252L generated in example 1 in the presence of NAD/NADH or carbaNAD/carbaNADH, a glucose dehydrogenase activity test was carried out for both enzymes.

Preparation of Reagent Solutions:

Tris buffer (0.1 M, pH 8.5; 0.2 M NaCl):

11.68 g NaCl (Sigma-Aldrich Company) and 12.11 g Tris (Sigma-Aldrich Company) were dissolved in about 900 ml double distilled water, adjusted with 1 N HCl to a pH of 8.5 and filled up to 1000 ml with double distilled water.

Dilution buffer (3.8 mM NAD; 0.1 M Tris, pH 8.5; 0.2 M NaCl):

250 mg NAD (Roche Company) was dissolved in 100 ml Tris buffer (0.1 M, pH 8.5; 0.2 M NaCl).

Glucose Solution:

2 g D(+) glucose monohydrate (Sigma-Aldrich Company) was dissolved in 10 ml double distilled water. The solution was ready-to-use after a standing time of 2 hours at room temperature and adjustment of the mutarotation equilibrium.

NAD Solution (15 Mm):

10 mg NAD (Roche Company) was dissolved in 1 ml double distilled water.

carbaNAD Solution (15 mM):

10 mg carbaNAD (Roche Company) was dissolved in 1 ml double distilled water.

Sample Preparation:

In order to prepare for the measurement, 10 mg of the enzyme to be examined was dissolved in 1 ml dilution buffer and kept for 60 min at room temperature, in order to allow a reconstitution. Subsequently it was diluted with dilution buffer to 0.12 to 0.23 U/ml.

Measurement Procedure:

In order to carry out the measurement 1.35 ml Tris buffer, 0.1 ml glucose solution and 0.05 ml NAD solution or 0.05 ml carbaNAD solution (each incubated to 25° C.) were pipetted into a plastic cuvette, mixed together and incubated to 25° C. in a cuvette carriage.

After the absorbance of the solution no longer changed (blank value), the reaction was started by introducing 0.025 ml sample into the cuvette, and the absorbance of the sample was monitored for a period of 5 min.

Measurement wavelength: 340 nm

Test volume: 1.525 ml

Path length: 1 cm

Temperature: 25° C.

Evaluation range: 1-5 min

Evaluation:

The activity of the respective enzyme in aqueous solution was evaluated using the following equation:

$$\text{activity} = (1.525 \times \Delta A/\text{min} \times \text{dilution factor})/(\epsilon_{340} \times 0.025 \times 1)/\text{U/ml}$$

in which:

ΔA=A$_1$−A$_0$=slope of the change in absorbance over time $\epsilon_{340}$=6.3 [1×mmol$^{-1}$×cm$^{-1}$]

The results of the determination are shown in table 2.

TABLE 2

Activity of wild type glucose dehydrogenase from *Bacillus subtilis* (WT-GlucDH) and of the double mutant GlucDH_E170K_K252L.

|  |  | WT-GlucDH | GlucDH_E170K_K252L |
|---|---|---|---|
| NAD | U/mg lyophilisate | 203 | 167 |
|  | U/mg enzyme | 484 | 270 |
|  | Km mM | 0.08 | 0.07 |
|  | V$_{max}$ (U/mg lyophilsate) | 122 | 144 |
| carbaNAD | U/mg lyophilisate | 3.4 | 2.3 |
|  | U/mg enzyme | 8.2 | 3.7 |
|  | % U/mg lyophilisate relative to NAD | 1.7% | 1.4% |
|  | Km mM | 0.3 | 1.4 |
|  | V$_{max}$ (U/mg lyophilisate) | 3 | 13 |

As shown in table 2, the activity of the system WT-glucDH/carbaNAD (8.2 U/mg enzyme) under standardized conditions in a cuvette is two orders of magnitude lower than the activity of the system WT-GlucDH/NAD (484 U/mg enzyme). Likewise it is found that the activity of the double mutant GlucDH_E170K_K252L in the presence of the artificial coenzyme carbaNAD is about two orders of magnitude lower (3.7 U/mg enzyme) than in the presence of the native coenzyme NAD (270 U/mg enzyme).

Example 4

Determination of the Kinetics of Wild Type Glucose Dehydrogenase from *Bacillus subtilis* (WT-GlucDH) and of the Double Mutant GlucDH_E170K_K252L in a Dry Reagent Layer Various test strips were prepared which either contained the native glucose dehydrogenase from *Bacillus subtilis* (WT-GlucDH) or the double mutant GlucDH_E170K_K252L prepared in example 1 in combination with NAD/NADH or carbaNAD/carbaNADH as the coenzyme, in order to determine the kinetics of enzymes.

Specifically, firstly a partial solution 1 consisting of 18.4 g 1 M phosphate buffer pH 7.0, 1.4 g Gantrez S97 (International Specialty Products Company), 2.94 g 16% NaOH solution, 0.34 g Mega 8 (Sigma-Aldrich Company), 0.039 g Geropon T77 (Rhone-Poulenc Company) and 1.90 g polyvinyl pyrrolidone 25000 (Fluka Company) was prepared for this purpose.

This partial solution was subsequently admixed with a partial solution 2 consisting of 0.50 g sodium chloride, 21.3 g double distilled water, 4.43 g Transpafill (Evonik Company) and 2.95 g Propiofan (BASF Company) as well as with a partial solution 3 stored overnight in a refrigerator, the latter consisting of 17.4 g 1 M phosphate buffer pH 7.0, 0.5 g sodium chloride, 14.35 g 2 M dipotassium hydrogen phosphate and the respective amounts of dehydrogenase, coenzyme and optionally bovine serum albumin (BSA; Roche Company) stated in each case in the following table 3. The enzymatically inactive bovine serum albumin was added to the formulation when reduced amounts of native dehydrogenase were used in order to keep the matrix properties of the test strip as constant as possible.

TABLE 3

Content of dehydrogenase and coenzyme in the test strips used.

| enzyme | mass enzyme (g) | lyophilisate activity (U/mg) | coenzyme | mass co-enzyme (g) | mass BSA (g) | kU/100 g mass |
|---|---|---|---|---|---|---|
| WT-GlucDH | 6.2 | 251 | NAD | 7.36 | 0 | 1556.2 |
| WT-GlucDH | 4.0 | 251 | NAD | 7.36 | 2.2 | 1004.0 |
| WT-GlucDH | 2.0 | 251 | NAD | 7.36 | 4.2 | 502.0 |
| WT-GlucDH | 1.0 | 251 | NAD | 7.36 | 5.2 | 251.0 |
| WT-GlucDH | 0.1 | 251 | NAD | 7.36 | 6.1 | 25.10 |
| GlucDH double mutant | 2.0 | 2.3 | carbaNAD | 2.1 | 0 | 4.60 |

The test strips obtained in this manner were measured on laboratory measuring instruments (self-made Roche Company) which comprised an excitation LED (375 nm) and conventional detectors (BPW34 blue-enhanced). The applied sample material was blood containing adjusted glucose values. The results of the determination are shown in FIGS. 1 and 2.

As shown in FIGS. 1A-1E, the kinetics of the conversion of glucose by wild type glucose dehydrogenase in the presence of NAD worsened with a decreasing enzyme content in the test strips and thus a decreasing enzyme activity. Thus, one would have expected that the kinetics of the conversion of glucose by means of the double mutant GlucDH_E170K_K252L in the presence of carbaNAD would yield even worse results due to the considerably lower enzyme activity of only 4.60 kU/100 g mass (see table 3).

Figure 2:
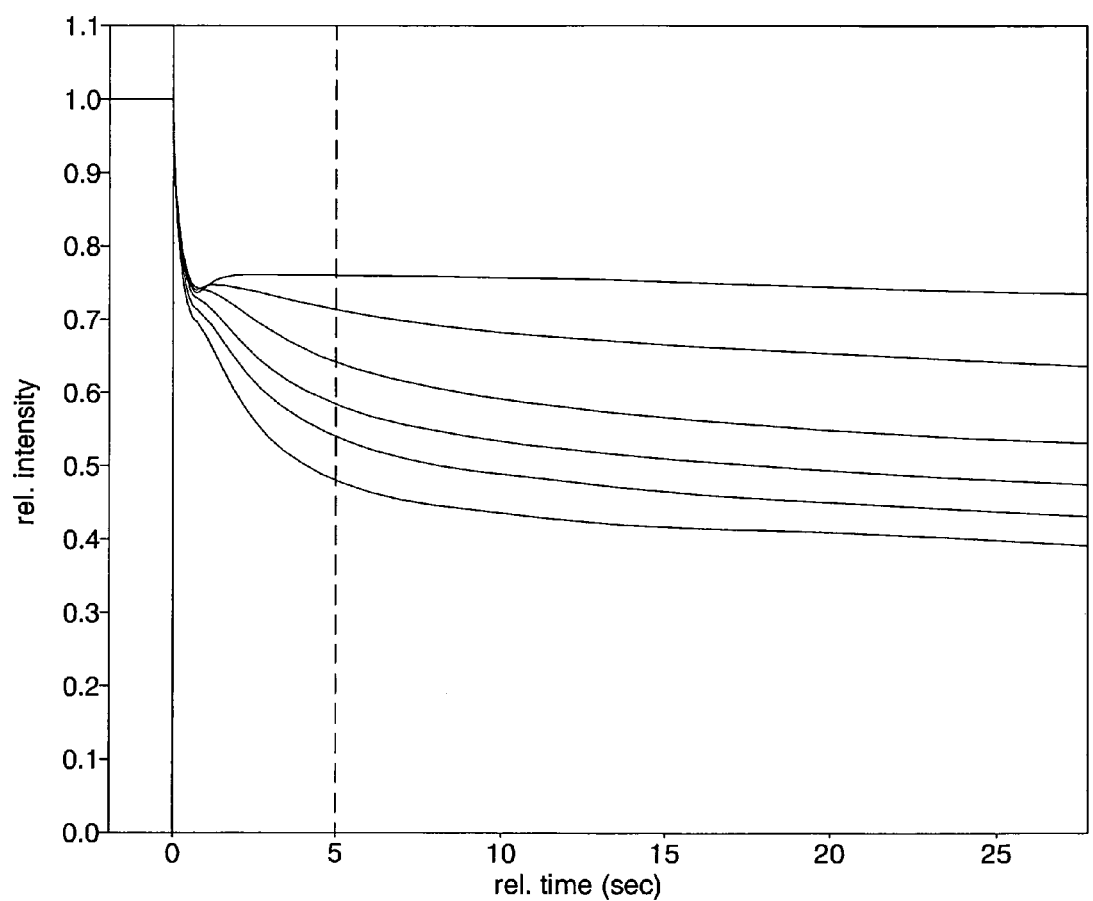
FIG. 2 is a graphical illustration of kinetics of a glucose dehydrogenase double mutant GlucDH_E170K_K252L obtained by mutation of wild type glucose dehydrogenase from Bacillus subtilis in the presence of carbaNAD/carbaNADH as the coenzyme at glucose concentrations of 0.0 mg/dl, 34.4 mg/dl, 141.2 mg/dl, 236.6 mg/dl, 333.8 mg/dl and 525.8 mg/dl (shown from top to bottom). Enzyme activity: 4.60 kU/100 g mass.

FIG. 2 shows the kinetics of the mutated glucose dehydrogenase obtained according to example 1 in the presence of carbaNAD as the coenzyme. As shown in FIG. 2, the impairment of the kinetics expected with a reduced enzyme activity does not occur. Rather, the double mutant exhibits better kinetics in the presence of carbaNAD than all formulations listed in table 3 which contain the corresponding wild type glucose dehydrogenase and the native coenzyme NAD.

If one takes into consideration the results described in examples 3 and 4, it appears that it is not the activity of the enzyme but rather the state of the complex formation between enzyme, coenzyme, reduced coenzyme, glucose and gluconolactone that is decisive for the turnover rate of glucose in dry reagent layers, which state of complex formation is apparently better in the case of the mutant prepared in example 1 with carbaNAD/carbaNADH than in the case of the wild type enzyme with native NAD/NADH.

Example 5

Detection of Ternary Complexes Consisting of Glucose Dehydrogenase, NADH and Glucose or Gluconolactone In order to check the existence of ternary complexes consisting of enzyme, reduced coenzyme and glucose or gluconolactone, experiments on the binding of the analyte based on the fluorescence properties of NADH were carried out in the cuvette test.

Figure 3:
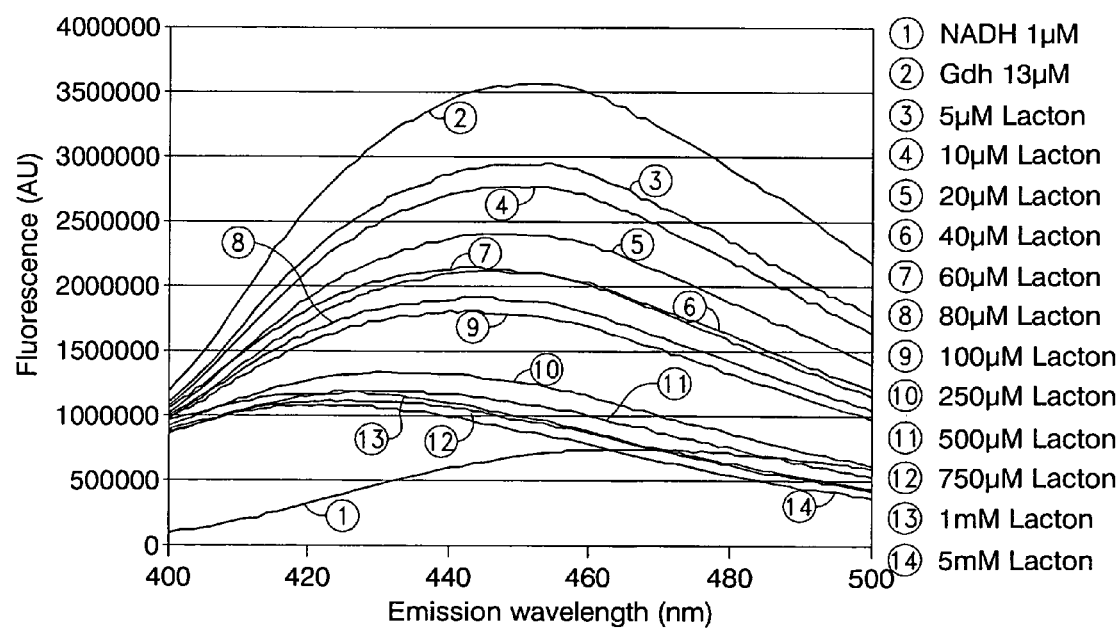
FIG. 3 is a graphical illustration of a fluorescence spectrum of the complex glucose dehydrogenase (GlucDH)/NADH before and after titration with gluconolactone.

For this purpose, 1 mg NADH (Roche Company) was dissolved in 1 ml phosphate buffer and the associated fluorescence spectrum was recorded. Subsequently, 10 mg wild type glucose dehydrogenase (GlucDH) from *Bacillus subtilis* was added whereupon the complex GlucDH-NADH known from the literature was formed, which complex, due to a considerably longer life time of NADH (3 ns compared to 0.4 ns in the free state), yielded a shifted emission maximum at 450 nm (see FIG. 3). Titration of this complex with gluconolactone lowered the fluorescence while, at the same time, shifting the emission maximum to 427 nm, the latter indicating the presence of a new complex that is the ternary complex GlucDH-NADH-gluconolactone (see FIG. 3).

Figure 4:
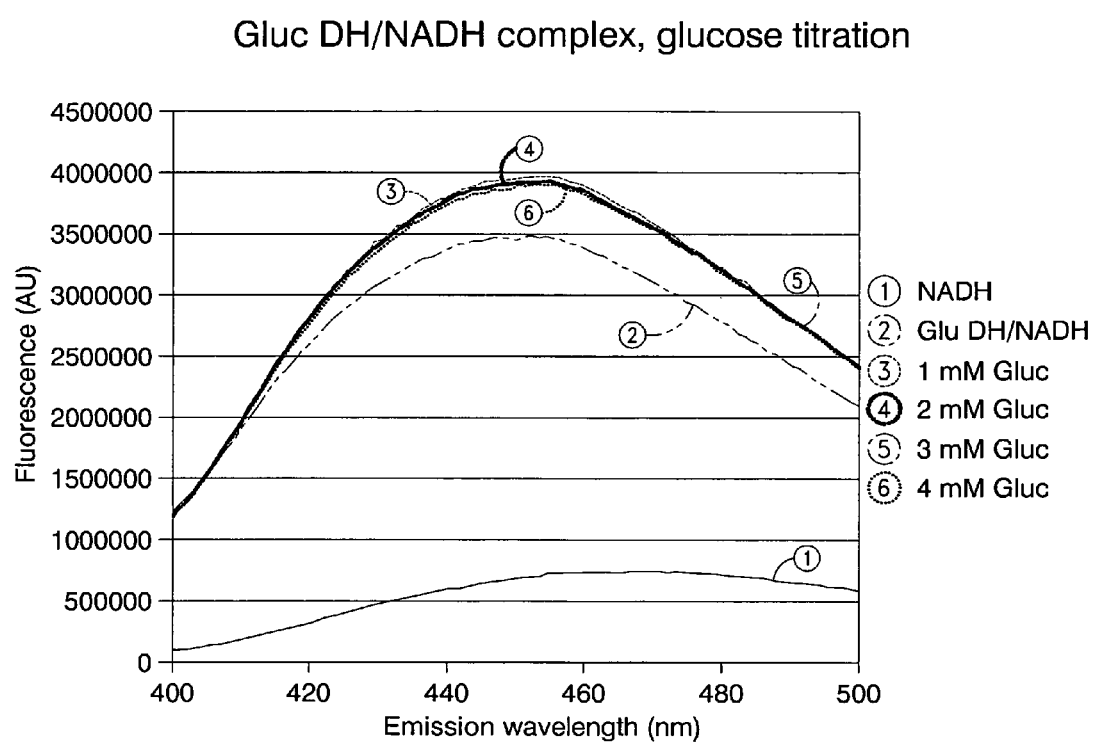
FIG. 4 is a graphical illustration of a fluorescence spectrum of the complex glucose dehydrogenase (GlucDH)/NADH before and after titration with glucose.

The lowering of the fluorescence which also corresponds to a shortening of the life time is presumably due to the rapid energy depletion by the redox pair NADH-gluconolactone. If the binary complex GlucDH-NADH is tritated with glucose, then an ineffective ternary GlucDH-NADH-glucose complex is formed which, due to the lack of a reducible species, cannot degrade energy in a special manner and therefore tends to exhibit an even longer life time and higher intensity at the same emission maximum (see FIG. 4).

If the cleavage of the ternary complex GlucDH-NADH-gluconolactone and thus the re-availability of the enzyme is decisive for the rate of conversion of glucose into gluconolactone in a dry reagent layer, addition of gluconolactone should slow down the conversion of glucose because additional gluconolactone (in addition to the gluconolactone formed in the reaction) should inhibit further enzyme complexes.

Figure 5A:
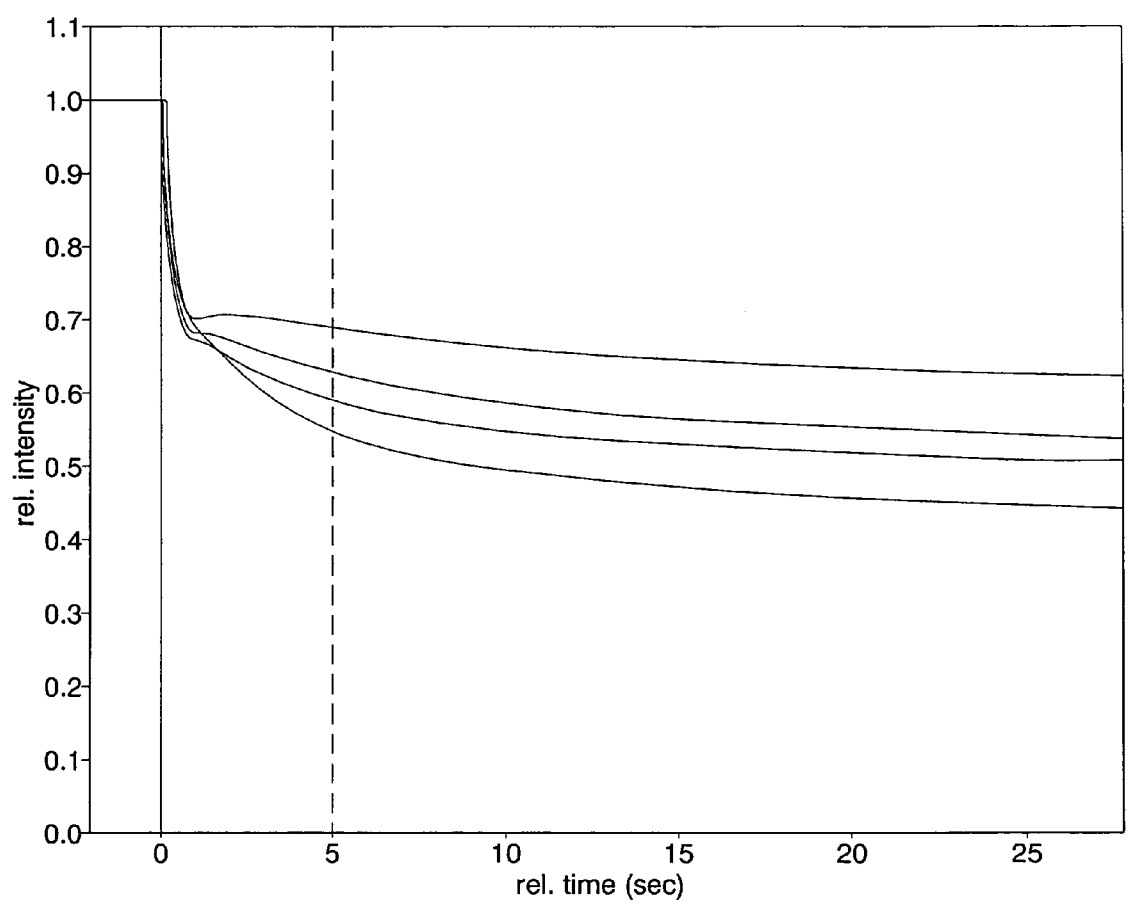
FIG. 5A: is a graphical illustration of kinetics without additionally added gluconolactone at glucose concentrations of 77.0 mg/dl, 207.0 mg/dl, 300.0 mg/dl and 505.0 mg/dl (shown from top to bottom).
Figure 5B:
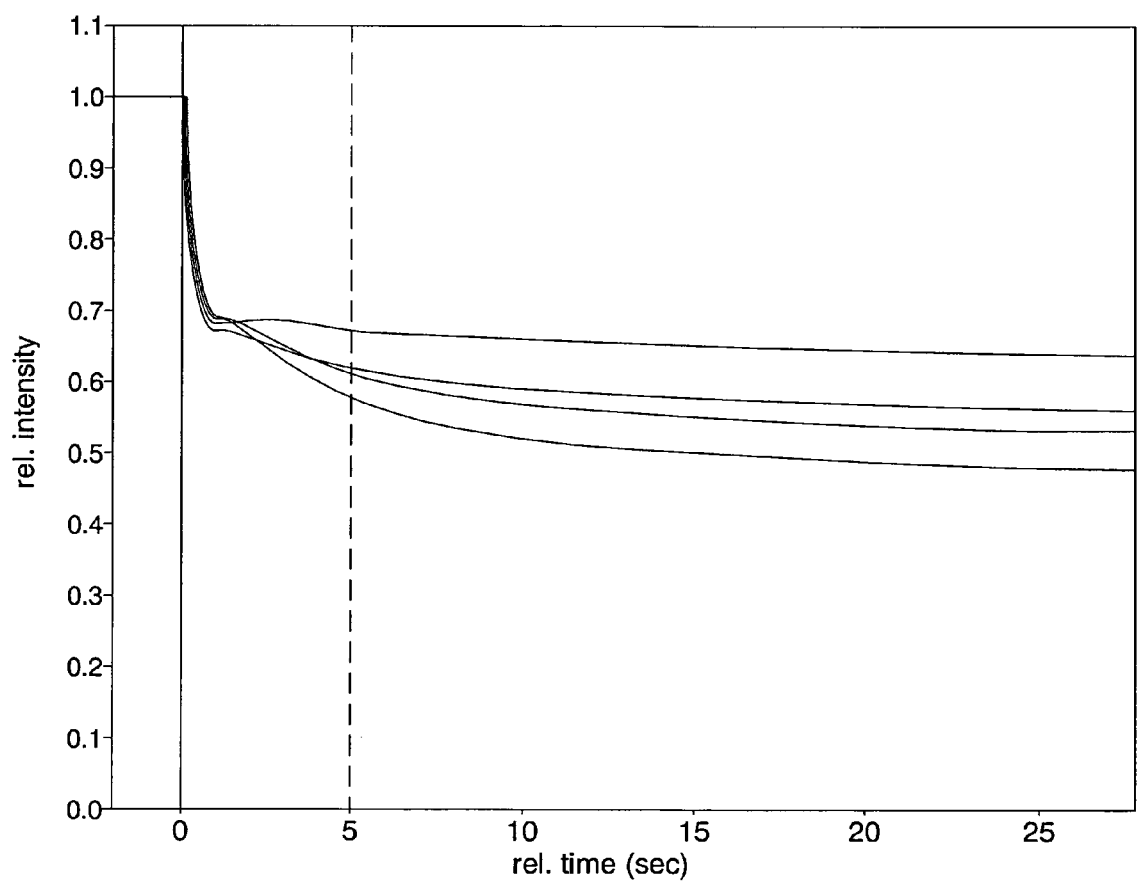
FIG. 5B: is a graphical illustration of kinetics with additionally added gluconolactone at glucose concentrations of 96.2 mg/dl, 274.0 mg/dl, 399.0 mg/dl and 600.0 mg/dl (shown from top to bottom).

This assumption was confirmed in a kinetic measurement in which blood was applied to a dry reagent layer according to example 4 of the present application in the absence (see FIG. 5A) or presence (see FIG. 5B) of gluconolactone. FIG. 5B shows a considerable slowing down of the conversion compared to the sample measured in FIG. 5A.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A method for determining an analyte, comprising:
  (a) contacting a sample containing the analyte with a diagnostic element comprising a dry reagent layer which contains:
    (i) a mutated glucose dehydrogenase obtained by mutating a wild type glucose dehydrogenase from *Bacillus megaterium* or *Bacillus subtilis*, wherein the wild type glucose dehydrogenase comprises an amino acid sequence selected from the group consisting of SEQ ID NOS:2, 3 and 4, and wherein the mutated glucose dehydrogenase includes mutations at positions 170 and 252 when compared to the amino acid sequence of SEQ ID NOS:2, 3 and 4, and wherein the mutation at position 170 is an amino acid substitution to lysine and the mutation at position 252 is an amino acid substitution to leucine; and
    (ii) an artificial coenzyme, wherein the artificial coenzyme is carbaNAD
  (b) determining at least one of analyte presence and an amount of the analyte.

2. The method according to claim 1, wherein the diagnostic test element includes a turnover rate of the analyte higher than a turnover rate of the analyte in a corresponding diagnostic element which comprises a corresponding wild type coenzyme instead of the artificial coenzyme.

3. The method according to claim 2, wherein the diagnostic test element includes a turnover rate of the analyte at least 20% higher than the turnover rate of the analyte in the corresponding diagnostic element.

4. The method according to claim 1, wherein the mutated glucose dehydrogenase has a reduced specific enzyme activity compared to a corresponding wild type dehydrogenase.

5. The method according to claim 1, wherein the mutated glucose dehydrogenase is a nicotinamide adenine dinucleotide (NAD/NADH)-dependent mutated glucose dehydrogenase or nicotinamide adenine dinucleotide phosphate (NADP/NADPH)-dependent mutated glucose dehydrogenase.

6. The method according to claim 1, wherein the mutated glucose dehydrogenase is obtained by mutation of the wild type glucose dehydrogenase from *Bacillus subtilis* having the amino acid sequence shown in SEQ ID NO:2.

7. The method according to claim 1, wherein the mutated glucose dehydrogenase has the amino acid sequence shown in SEQ ID NO:1.

8. The method according to claim 1, wherein the diagnostic element is one of a test tape, a test disk, a test pad, a test strip and a test strip drum.

9. The method according to claim 1, which further includes photometrically or fluorometrically determining at least one of the analyte presence and the amount of the analyte.

10. A diagnostic element for determining an analyte, comprising a dry reagent layer which contains:
  (a) a mutated dehydrogenase obtained by mutating a wild type glucose dehydrogenase comprising an amino acid sequence selected from the group consisting of SEQ ID NOS:2, 3 and 4, and wherein the mutated glucose dehydrogenase includes mutations at positions 170 and 252 when compared to the amino acid sequence of SEQ ID NOS:2, 3 and 4, and wherein the mutation at position 170 is an amino acid substitution to lysine and the mutation at position 252 is an amino acid substitution to leucine, and
  (b) an artificial coenzyme, wherein the artificial coenzyme is carbaNAD.

11. The diagnostic element according to claim 10, wherein the mutated dehydrogenase has the amino acid sequence shown in SEQ ID NO:1.

12. The method according to claim 1, wherein the mutated glucose dehydrogenase is obtained by mutation of the wild type glucose dehydrogenase from *Bacillus megaterium* having the amino acid sequence shown in SEQ ID NO:3.

13. The method according to claim 1, wherein the mutated glucose dehydrogenase is obtained by mutation of the wild type glucose dehydrogenase from *Bacillus subtilis* having the amino acid sequence shown in SEQ ID NO:4.

* * * * *

SEQUENCE LISTING

```
<160> NUMBER OF SEQ ID NOS: 4

<210> SEQ ID NO 1
<211> LENGTH: 261
<212> TYPE: PRT
<213> ORGANISM: Artificial Sequence
<220> FEATURE:
<223> OTHER INFORMATION: Mutant of glucose dehydrogenase from Bacillus
      subtilis
<220> FEATURE:
<221> NAME/KEY: MUTAGEN
<222> LOCATION: (170)..(170)
<220> FEATURE:
<221> NAME/KEY: MUTAGEN
<222> LOCATION: (252)..(252)

<400> SEQUENCE: 1

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190
```

```
Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 2
<211> LENGTH: 261
<212> TYPE: PRT
<213> ORGANISM: Bacillus subtilis

<400> SEQUENCE: 2

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
            260

<210> SEQ ID NO 3
<211> LENGTH: 261
<212> TYPE: PRT
<213> ORGANISM: Bacillus megaterium
```

-continued

```
<400> SEQUENCE: 3

Met Tyr Lys Asp Leu Glu Gly Lys Val Val Ile Thr Gly Ser Ser
1               5                   10                  15

Thr Gly Leu Gly Lys Ser Met Ala Ile Arg Phe Ala Thr Glu Lys Ala
                20                  25                  30

Lys Val Val Asn Tyr Arg Ser Lys Glu Asp Glu Ala Asn Ser Val
            35                  40                  45

Leu Glu Glu Ile Lys Lys Val Gly Gly Glu Ala Ile Ala Val Lys Gly
        50                  55                  60

Asp Val Thr Val Glu Ser Asp Val Ile Asn Leu Val Gln Ser Ala Ile
65                  70                  75                  80

Lys Glu Phe Gly Lys Leu Asp Val Met Ile Asn Asn Ala Gly Leu Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

Lys Tyr Phe Val Glu Asn Asp Ile Lys Gly Thr Val Ile Asn Met Ser
130                 135                 140

Ser Val His Glu Lys Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
210                 215                 220

Ala Ala Val Ala Ala Trp Leu Ala Ser Ser Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 4
<211> LENGTH: 261
<212> TYPE: PRT
<213> ORGANISM: Bacillus subtilis

<400> SEQUENCE: 4

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95
```

-continued

```
Asn Pro Val Pro Ser His Glu Met Pro Leu Lys Asp Trp Asp Lys Val
        100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                     150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                     230                 235                 240

Gly Ile Thr Leu Phe Ala Asp Gly Gly Met Thr Gln Tyr Pro Ser Phe
                245                 250                 255

Gln Ala Gly Arg Gly
            260
```